United States Patent
Dubhashi

(10) Patent No.: US 12,213,789 B2
(45) Date of Patent: *Feb. 4, 2025

(54) IDENTIFYING PATIENTS SUITED FOR RENAL DENERVATION THERAPY

(71) Applicant: Medtronic Ireland Manufacturing Unlimited Company, Dublin (IE)

(72) Inventor: Abhijeet Dubhashi, Cotati, CA (US)

(73) Assignee: Medtronic Ireland Manufacturing Unlimited Company, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 18/308,382

(22) Filed: Apr. 27, 2023

(65) Prior Publication Data

US 2023/0263443 A1    Aug. 24, 2023

Related U.S. Application Data

(63) Continuation of application No. 16/394,438, filed on Apr. 25, 2019, now Pat. No. 11,672,456.

(60) Provisional application No. 62/663,394, filed on Apr. 27, 2018.

(51) Int. Cl.
*A61B 5/20* (2006.01)
*A61B 5/00* (2006.01)
*A61B 5/021* (2006.01)
*G06N 3/08* (2023.01)
*A61B 5/02* (2006.01)

(Continued)

(52) U.S. Cl.
CPC .......... *A61B 5/201* (2013.01); *A61B 5/02108* (2013.01); *A61B 5/6824* (2013.01); *A61B 5/7267* (2013.01); *G06N 3/08* (2013.01); *A61B 5/02007* (2013.01); *G16H 10/60* (2018.01); *G16H 50/30* (2018.01)

(58) Field of Classification Search
USPC .......................... 382/128, 155–156; 600/301
See application file for complete search history.

(56) References Cited

U.S. PATENT DOCUMENTS

| 11,672,456 B2* | 6/2023 | Dubhashi ................. | G06N 3/08 706/15 |
| 2016/0113699 A1* | 4/2016 | Sverdlik ................ | A61N 7/022 606/27 |
| 2017/0347936 A1* | 12/2017 | Stahmann .......... | A61B 5/14865 |

(Continued)

*Primary Examiner* — Ishrat I Sherali
(74) *Attorney, Agent, or Firm* — Shumaker & Sieffert, P.A.

(57) ABSTRACT

Example devices, systems, and techniques predict renal denervation efficacy for reducing hypertension in a patient based on pulse information. For example, a system may include processing circuitry configured to obtain pulse information representative of pulses from both wrists of a patient, obtain a plurality of values representative of respective patient metrics for the patient, and apply the pulse information and the plurality of values to a deep learning model trained to represent a relationship of the pulse information and the patient metrics to an efficacy of renal denervation in reducing hypertension. In some examples, responsive to applying the pulse information and the plurality of values to the deep learning model, the processing circuitry obtains, from the deep learning model, a score indicative of renal denervation efficacy in reducing hypertension for the patient, and generates a graphical user interface comprising a graphical representation of the score for the patient.

20 Claims, 5 Drawing Sheets

(51) Int. Cl.
　　　*G16H 10/60*　　　(2018.01)
　　　*G16H 50/30*　　　(2018.01)

(56) References Cited

U.S. PATENT DOCUMENTS

| | | | |
|---|---|---|---|
| 2019/0290139 A1* | 9/2019 | Sio | A61B 5/02125 |
| 2021/0383908 A1* | 12/2021 | Foin | G16H 20/00 |
| 2023/0233168 A1* | 7/2023 | Chen | A61B 5/6851 |
| | | | 600/424 |

* cited by examiner

IDENTIFYING PATIENTS SUITED FOR RENAL DENERVATION THERAPY

This application is a continuation of U.S. patent application Ser. No. 16/394,438, filed 25 Apr. 2019, which claims the benefit of U.S. Provisional Patent Application No. 62/663,394, filed 27 Apr. 2018; the entire content of each application is incorporated herein by reference in its entirety.

TECHNICAL FIELD

The present disclosure relates to, in some examples, systems and techniques for identifying candidates for renal denervation therapy.

BACKGROUND

Overstimulated or excessively active nerves may result in adverse effects to organs or tissue served by the respective nerves. For example, for some patients, heart, circulatory, or renal disease may be associated with pronounced cardiorenal sympathetic nerve hyperactivity. Stimulation of the renal sympathetic nerves can cause one or more of an increased renin release, increased sodium ($Na^+$) reabsorption, or a reduction of renal blood flow. The kidneys may be damaged by direct renal toxicity from the release of sympathetic neurotransmitters (such as norepinephrine) in the kidneys in response to high renal nerve stimulation. Additionally, the increase in release of renin may ultimately increase systemic vasoconstriction, aggravating hypertension. Such conditions may be mitigated by modulating the activity of overactive nerves.

SUMMARY

The present disclosure describes devices, systems, and techniques for predicting renal denervation efficacy in reducing hypertension in a patient based on pulse information from one or more wrists of the patient. A system may use one or more sensors to generate pulse information from certain locations of the wrists of the patient, as this pulse information may indicate the contribution of the kidneys to hypertension of the patient. Using a deep learning model trained to predict renal denervation efficacy based on pulse information, the system may apply the pulse information obtained from the one or more sensors, and other patient metrics obtained from the patient, to the deep learning model and obtain a score from the deep learning model indicative of renal denervation efficacy in reducing hypertension for the patient. This score may be a probability that the patient would achieve a target reduction in hypertension from renal denervation therapy. In some examples, the processing circuitry may generate a graphical user interface that indicates the score and present the graphical user interface via a display.

In some examples, the disclosure describes a system that includes a memory configured to store a deep learning model, the deep learning model trained to represent a relationship between patient metrics and renal denervation efficacy in reducing hypertension, and processing circuitry configured to obtain pulse information representative of pulses from both wrists of a patient, obtain a plurality of values representative of respective patient metrics for the patient, apply the pulse information and the plurality of values to the deep learning model from the memory, responsive to applying the pulse information and the plurality of values to the deep learning model, obtain, from the deep learning model, a score indicative of renal denervation efficacy in reducing hypertension for the patient, and generate a graphical user interface comprising a graphical representation of the score for the patient.

In some examples, the disclosure describes a method that includes obtaining, by processing circuitry, pulse information representative of pulses from both wrists of a patient, obtaining, by the processing circuitry, a plurality of values representative of respective patient metrics for the patient, applying, by the processing circuitry, the pulse information and the plurality of values to a deep learning model stored in a memory, the deep learning model trained to represent a relationship between the patient metrics and renal denervation efficacy in reducing hypertension, responsive to applying the pulse information and the plurality of values to the deep learning model, obtaining, by the processing circuitry and from the deep learning model, a score indicative of renal denervation efficacy in reducing hypertension for the patient, and generating, by the processing circuitry, a graphical user interface comprising a graphical representation of the score for the patient.

In some examples, the disclosure describes a non-transitory computer-readable medium that includes instructions that, when executed by at least one processor, causes the at least one processor to obtain pulse information representative of pulses from both wrists of a patient, obtain a plurality of values representative of respective patient metrics for the patient, apply the pulse information and the plurality of values to the deep learning model from a memory, the deep learning model trained to represent a relationship between patient metrics and renal denervation efficacy in reducing hypertension, responsive to applying the pulse information and the plurality of values to the deep learning model, obtain, from the deep learning model, a score indicative of renal denervation efficacy in reducing hypertension for the patient, and generate a graphical user interface comprising a graphical representation of the score for the patient.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

Reference is made to the attached drawings, wherein elements having the same reference numeral designations represent similar elements throughout and wherein.

DETAILED DESCRIPTION

Figure 1:
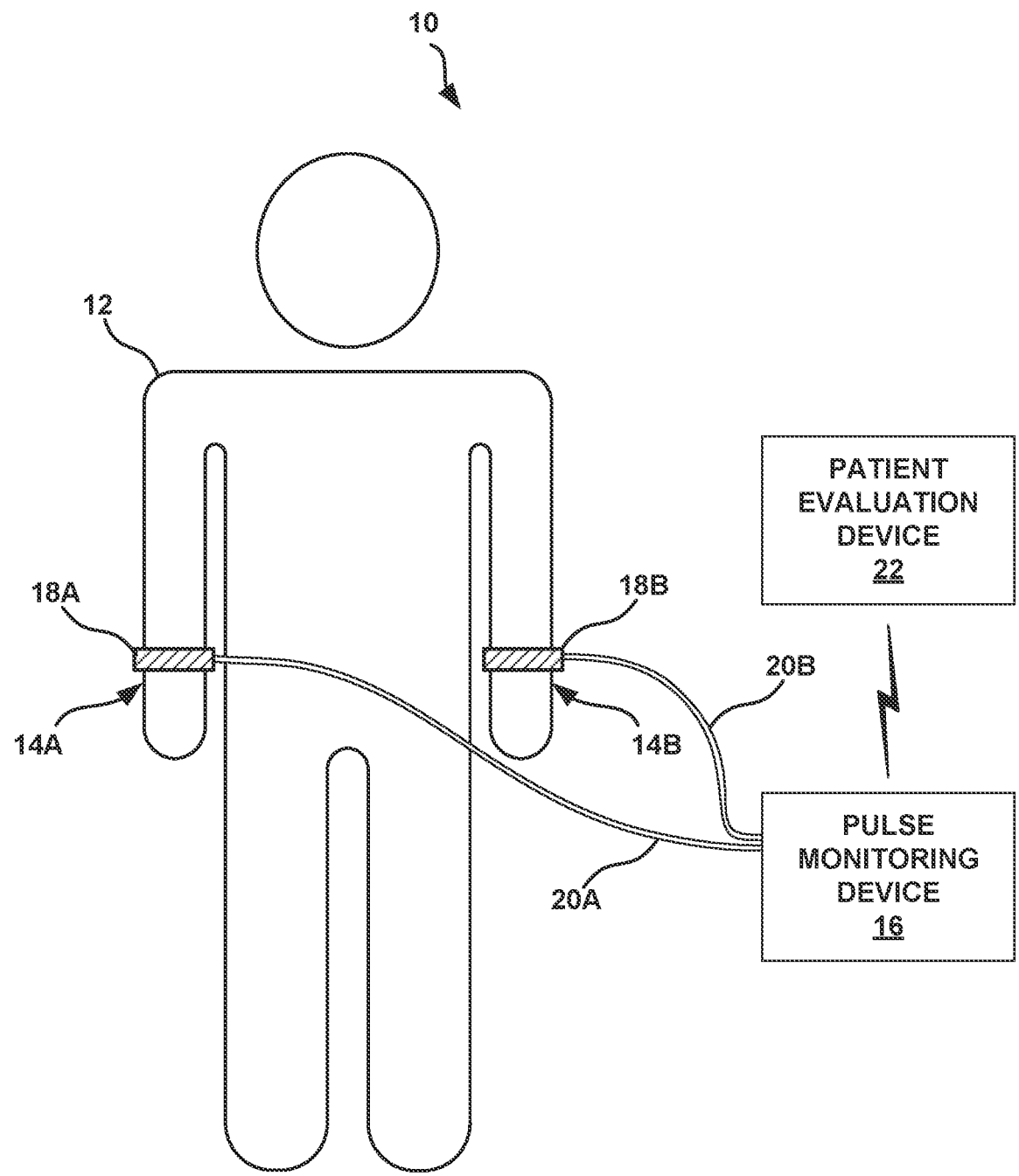
FIG. 1 is a conceptual illustration of an example system including a pulse monitoring device and a patient evaluation device.

As described herein, devices, systems, and techniques are related to obtaining pulse information from a patient and predicting the efficacy of renal denervation in reducing hypertension in a patient based on the pulse information. Denervation therapy may be used to render a nerve inert, inactive, or otherwise completely or partially reduced in function, such as by ablation or lesioning of the nerve. Following denervation, there may be a reduction or even prevention of neural signal transmission along the target nerve. Denervating an overactive nerve may provide a therapeutic benefit to a patient. For example, renal denervation may mitigate symptoms associated with renal sympathetic nerve overstimulation. Denervation therapy may include delivering electrical and/or thermal energy to a target nerve, and/or by delivering a chemical agent to a target nerve. In the case of renal denervation therapy, the denervation energy or chemical agents can be delivered, for example, via a therapy delivery device (e.g., a catheter) disposed in a blood vessel (e.g., the renal artery) proximate the renal nerve.

The renal sympathetic nervous system has been identified as a major contributor to the complex pathophysiology of hypertension, or elevated systemic blood pressure. Therefore, renal denervation may reduce renal sympathetic nerve overstimulation and cause a reduction in systemic blood pressure as a treatment for hypertension. In some patients, renal denervation may reduce systolic blood pressure in a range of approximately 5 millimeters of mercury (mmHg) to 30 mmHg. However, renal denervation may not reduce systemic blood pressure for other patients. For example, if the kidneys of a patient are not contributing to the pathophysiology of hypertension, renal denervation may not provide relief from hypertension for that patient.

The present disclosure describes devices, systems, and techniques related to predicting the efficacy of renal denervation in reducing hypertension for a patient. For example, a system may generate a score indicative of renal denervation efficacy in reducing hypertension for a patient, where the score is determined based on pulse information derived from the patient. With every contraction of the left ventricle of the heart, the left ventricle ejects blood to generate a pressure pulse that travels throughout the arteries of the patient. This pulse is detectable at the wrist of the patient, but characteristics of the pulse at different locations along the wrist and may provide information regarding different organs. For example, pulse characteristics indicative of the kidneys may be obtained from a location of the wrists further from the hand than locations indicative of the lung and spleen on the right wrist and locations indicative of the heart and liver on the left wrist.

Pulse sensors placed on the wrists of the patient may generate the pulse information representative of the blood pressure pulse. In one example, each pulse sensor may include three sensing modules arranged to be disposed at different positions along the length of the wrist to detect the pulse at respective locations of the wrist. The pulse sensors may include any suitable type of sensor, such as spectrophotometric sensors and/or pneumatic pulse sensors, that are configured to generate signals representative of the pulse that may include one or more characteristics of the pulse, such as a pulse rate, a pulse amplitude, a pulse rate variability, a pulse waveform morphology, or a pulse echo. The pulse sensors may transmit the generated pulse information to a pulse monitoring device for conditioning and/or analysis of the pulse information, or the pulse sensors may transmit the pulse information directly to a patient evaluation device for patient evaluation. This use of pulse information generated from pulse waves detected from the wrists of a patient to predict the efficacy of renal denervation in reducing hypertension for a patient is an unconventional use of pulse detection sensors.

A patient evaluation device may utilize machine learning, such as a deep learning algorithm or model (e.g., a neural network or deep belief network), to generate a score indicative of renal denervation efficacy in reducing hypertension for the patient. The patient evaluation device may train a deep learning model to represent a relationship of pulse information and other patient metrics of patients to the efficacy of renal denervation therapy in reducing hypertension. For example, the patient evaluation device may train the deep learning model using pulse information, patient metrics, and renal denervation efficacy from other patients. In some examples, the patient evaluation device may train the deep leaning model by adjusting the weights of a hidden layer of a neural network model to balance the contribution of each input (e.g., characteristics of the pulse information and/or the values of each patient metric) according to how effective renal denervation was in treating the hypertension of each patient.

Once the deep learning model is trained, the patient evaluation device may obtain and apply data, such as the pulse information from the pulse sensors for a patient and a plurality of values representative of respective patient metrics for the patient, to the trained deep learning model. Example patient metrics may include an age of the patient, a gender of the patient, an ethnic background of the patient, a weight of the patient, a height of the patient, a diet of the patient, an activity level of the patient, or a stress level of the patient. The pulse information may include one or more characteristics of the pulse at certain locations of the patient's wrist. The output of the deep learning model may include the score that indicates whether or not the patient would be a suitable candidate for renal denervation therapy. For example, the score may be a probability that the patient would achieve a target reduction in hypertension in response to receiving renal denervation therapy. In some examples, the score may be indicative of the magnitude of the reduction in systemic blood pressure that the patient may realize after renal denervation therapy. The patient evaluation device may display the score to a clinician to aid in determining whether or not the patient should receive renal denervation therapy.

Generally, the pulse information described herein is derived from the radial pulse detected from the radial artery of the patient. In some examples, the pulse information may instead, or additionally, be derived from the ulnar pulse from the ulnar artery on the opposing side of the wrist. Pulse information may also, or alternatively, be obtained from other arteries in the patient. The examples herein are directed to human patients. However, the techniques and systems described herein may also be used to screen non-human mammals for renal denervation therapy in other examples.

FIG. 1 is a conceptual illustration of an example system 10 including a pulse monitoring device 16, sensors 18A and 18B (collectively "sensors 18"), and a patient evaluation device 22. Each of sensors 18 may be configured to detect blood pressure pulses from respective wrists 14A and 14B (collectively "wrists 14") of patient 12. Using pulse information generated by sensors 18, patient evaluation device 22 may be configured to generate a score indicative of the predicted efficacy of renal denervation in reducing blood pressure as a treatment for hypertension of patient 12. As described herein, the efficacy of renal denervation in reducing blood pressure may be a predicted or estimated efficacy based on the inputs to the system, such as pulse information and other patient metrics representative of patient 12.

Each kidney of patient 12 is innervated by the renal plexus RP, which is intimately associated with the renal artery. The renal plexus RP is an autonomic plexus that surrounds the renal artery and is embedded within the adventitia of the renal artery. The renal plexus RP extends along the renal artery until it arrives at the substance of the kidney. Fibers contributing to the renal plexus RP arise from the celiac ganglion, the superior mesenteric ganglion, the aorticorenal ganglion and the aortic plexus. The renal plexus RP, also referred to as the renal nerve, is predominantly comprised of sympathetic components. There is no (or at least very minimal) parasympathetic innervation of the kidneys.

Preganglionic neuronal cell bodies are located in the intermediolateral cell column of the spinal cord. Preganglionic; axons pass through the paravertebral ganglia (they do not synapse) to become the lesser splanchnic nerve, the least splanchnic nerve, first lumbar splanchnic nerve, second lumbar splanchnic nerve, and travel to the celiac ganglion, the superior mesenteric ganglion, and the aorticorenal ganglion. Postganglionic neuronal cell bodies exit the celiac ganglion, the superior mesenteric ganglion, and the aorticorenal ganglion to the renal plexus RP and are distributed to the renal vasculature.

Messages travel through the sympathetic nervous system (SNS) in a bidirectional flow. Efferent messages may trigger changes in different parts of the body simultaneously. For example, the sympathetic nervous system may accelerate heart rate; widen bronchial passages; decrease motility (movement) of the large intestine; constrict blood vessels increase peristalsis in the esophagus; cause pupil dilation, piloerection (goose bumps) and perspiration (sweating); and raise blood pressure. Afferent messages carry signals from various organs and sensory receptors in the body to other organs and, particularly, the brain.

Hypertension, heart failure, and chronic kidney disease are a few of many disease states that can result from chronic activation of the SNS, especially the renal sympathetic nervous system. Chronic activation of the SNS is a maladaptive response that drives the progression of these disease states.

The renal sympathetic nervous system has been identified as a major contributor to the complex pathophysiology of hypertension, states of volume overload (such as heart failure), and progressive renal disease, both experimentally and in humans. Studies employing radiotracer dilution methodology to measure overflow of norepinephrine from the kidneys to plasma revealed increased renal norepinephrine (NE) spillover rates in patients with essential hypertension, particularly so in young hypertensive subjects, which in concert with increased NE spillover from the heart, is consistent with the hemodynamic profile typically seen in early hypertension and characterized by an increased heart rate, cardiac output, and renovascular resistance. Essential hypertension can be neurogenic, often accompanied by pronounced sympathetic nervous system overactivity.

Activation of cardiorenal sympathetic nerve activity is even more pronounced in heart failure, as demonstrated by an exaggerated increase of NE overflow from the heart and the kidneys to plasma in this patient group. In line with this notion is the recent demonstration of a strong negative predictive value of renal sympathetic activation on all-cause mortality and heart transplantation in patients with congestive heart failure, which is independent of overall sympathetic activity, glomerular filtration rate, and left ventricular ejection fraction. These findings support the notion that treatment regimens (that are designed to reduce renal sympathetic stimulation have the potential to improve survival in patients with heart failure.

Both chronic and end stage renal disease are characterized by heightened sympathetic nervous activation. In patients with end stage renal disease, plasma levels of norepinephrine above the median have been demonstrated to be predictive for both all-cause death and death from cardiovascular disease. This is also true for patients suffering from diabetic or contrast nephropathy. There is compelling evidence suggesting that sensory afferent signals originating from the diseased kidneys are major contributors to initiating and sustaining elevated central sympathetic outflow in this patient group; this facilitates the occurrence of the well-known adverse consequences of chronic sympathetic over activity, such as hypertension, left ventricular hypertrophy, ventricular arrhythmias, sudden cardiac death, insulin resistance, diabetes, and metabolic syndrome.

Sympathetic nerves to the kidneys terminate in the blood vessels, the juxtaglomerular apparatus and the renal tubules. Stimulation of the renal sympathetic nerves can cause increased renin release, increased sodium (Na+) reabsorption, and a reduction of renal blood flow. These components of the neural regulation of renal function are considerably stimulated in disease states characterized by heightened sympathetic tone and clearly contribute to the rise in blood pressure in hypertensive patients. The reduction of renal blood flow and glomerular filtration rate as a result of renal sympathetic efferent stimulation may be a likely cornerstone of the loss of renal function in cardio-renal syndrome, which is renal dysfunction as a progressive complication of chronic heart failure, with a clinical course that typically fluctuates with the patient's clinical status and treatment. Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release), and diuretics (intended to counter the renal sympathetic mediated sodium and water retention). However, the current pharmacologic strategies have limitations including limited efficacy, compliance issues, side effects and others.

The kidneys communicate with integral structures in the central nervous system via renal sensory afferent nerves. Several forms of "renal injury" may induce activation of sensory afferent signals. For example, renal ischemia, reduction in stroke volume or renal blood flow, or an abundance of adenosine enzyme may trigger activation of afferent neural communication.

Neural efferent and afferent communication occurs between the brain and kidneys. Afferent communication might be from the kidney to the brain or might be from one kidney to the other kidney (via the central nervous system). These afferent signals are centrally integrated and may result in increased sympathetic outflow. This sympathetic drive is directed towards the kidneys, thereby activating the renin-angiotensin-aldosterone system (RAAS) and inducing increased renin secretion, sodium retention, volume retention and vasoconstriction. Central sympathetic over activity also impacts other organs and bodily structures innervated by sympathetic nerves such as the heart and the peripheral vasculature, resulting in the described adverse effects of sympathetic activation, several aspects of which also contribute to the rise in blood pressure.

The physiology therefore indicates that (i) modulation of tissue with efferent sympathetic nerves may reduce inappropriate renin release, salt retention, and reduction of renal blood flow, and that (ii) modulation of tissue with afferent sensory nerves may reduce the systemic contribution to hypertension and other disease states associated with increased central sympathetic tone through its direct effect on the posterior hypothalamus as well as the contralateral kidney. In addition to the central hypotensive effects of afferent renal denervation, a desirable reduction of central sympathetic outflow to various other sympathetically innervated organs such as the heart and the vasculature is anticipated.

As provided above, renal denervation may be valuable in the treatment of several clinical conditions characterized by increased overall and particularly renal sympathetic activity such as hypertension, metabolic syndrome, insulin resistance, diabetes, left ventricular hypertrophy, chronic end stage renal disease, inappropriate fluid retention in heart failure, cardio-renal syndrome, and sudden death. Because the reduction of afferent neural signals contributes to the systemic reduction of sympathetic tone/drive, renal denervation might also be useful in treating other conditions associated with systemic sympathetic hyperactivity. Accordingly, renal denervation may also benefit other organs and bodily structures innervated by sympathetic nerves. For example, a reduction in central sympathetic drive may reduce the insulin resistance that afflicts people with metabolic syndrome and Type II diabetics. Additionally, patients with osteoporosis are also sympathetically activated and might also benefit from the down regulation of sympathetic drive that accompanies renal denervation.

Although renal denervation may be effective for some patients in treating conditions characterized by increased renal sympathetic activity, such as hypertension, not all patients may benefit from renal denervation. The techniques described herein are directed to screening patients that may be candidates for renal denervation as a treatment for hypertension. However, these techniques may also be used to screen patients for renal denervation intended to treat other conditions that may be associated with increased renal sympathetic activity in other examples. In any case, a patient evaluation system, such as patient evaluation device 22, may be configured to determine a score or other output that indicates whether or not a particular patient may be a suitable candidate for renal denervation as a therapy directed to reducing systemic blood pressure, and treating hypertension, for that particular patient. For example, the score may indicate whether the kidneys of patient 12 are contributing to the pathophysiology of hypertension, such that renal denervation may help manage the diagnosed hypertension of patient 12 (e.g., reduce systemic blood pressure values).

System 10 may collect or obtain information about patient 12 in order to generate the score that is indicative of whether or not patient 12 may receive any relief from hypertension as a result of renal denervation therapy, or the extent to which patient 12 renal denervation therapy may be efficacious in reducing hypertension of patient 12. System 10 may include a memory (e.g., memory 54 of FIG. 3) that is configured to store a deep learning model such as a neural network model, a deep belief network, or other deep learning algorithm. The deep learning model is trained, by system 10 or another computing system, to represent a relationship of pulse information and patient metrics to renal denervation efficacy in reducing hypertension. This relationship may be between the patient pulse information and patient metrics of respective patients to actual renal denervation efficacy for the respective patients. In other words, prior patient information may be used to train the deep learning model that is used to predict renal denervation efficacy for patients that have not yet received the renal denervation therapy. Processing circuitry (e.g., processing circuitry 50 of patient evaluation device 22 shown in FIG. 3) may be configured to obtain pulse information representative of pulses from both of wrists 14 of patient 12. The processing circuitry may also be configured to obtain a plurality of values representative of respective patient metrics for patient 12 and apply the pulse information and the plurality of values to the deep learning model from the memory. Responsive to applying the pulse information and the plurality of values to the deep learning model, the processing circuitry may obtain, from the deep learning model, a score indicative of predicted renal denervation efficacy in reducing hypertension for patient 12. System 10 may then generate a graphical user interface that includes a graphical representation of the score for patient 12, whereby the score indicates whether or not renal denervation could be an effective treatment for the hypertension experienced by patient 12.

As discussed above, system 10 may use pulse information to determine the score indicative of renal denervation efficacy. For example, system 10 may obtain pulse information from wrists 14. Sensors 18A and 18B may be attached to respective wrists 14A and 14B of patient 12 and generate pulse signals (e.g., a type of pulse information) representative of the blood pressure pulses traveling through the respective radial arteries of wrists 14. Sensors 18 may each generate an analog signal and/or or digital signal that is representative of the blood pressure pulse. For example, the analog pulse signal may be a waveform that represents the varying magnitude of the pulse over time. The analog pulse signal may be representative of the blood pressure itself, or may increase and decrease with the actual blood pressure at the point of measurement. In some examples, sensors 18 may generate a signal which may include samples of the pulse over time, a data point whenever the pulse exceeds one or more thresholds (e.g., indicating when a pulse happens to indicate pulse rate), or some other non-continuous signal indicative of some sensed event related to the pulse of patient 12.

Sensors 18 may each by configured to generate pulse information. For example, sensor 18A may be configured to generate first pulse information representative of pulses from right wrist 14A of patient 12 and transmit the first pulse information to the processing circuitry of pulse monitoring device 16. In addition, sensor 18B may be configured to generate second pulse information representative of pulses from a left wrist 14B of patient 12 and transmit the second pulse information to the processing circuitry of pulse monitoring device 16. Pulse monitoring device 16 may be configured to control sensors 18 to generate pulse information for the same time period such that the pulse information is reflective of some or all of the pulse waves resulting from the same ventricular contractions. In other examples, the pulse information from each of wrists 14 may not need to be reflective of the same ventricular contractions. In this case, pulse monitoring device 16 may receive pulse information from each wrist 14 generated by sensors 18 at different times, or a single sensor 18A may be used to generate pulse information from wrist 14A and then be moved to wrist 14B to subsequently generate pulse information from wrist 14B.

Sensors 18 may include one or more sensing modules configured to transform the pulse occurring within patient 12 to a transmittable pulse signal. For example, sensors 18 may include one or more pneumatic pulse sensors that are configured to generate a signal in response to the pulse in the wrist applying a force against the pulse sensor. A pneumatic pulse sensor may include an air chamber disposed against the wrist at a location near the radial artery. Therefore, blood pressure pulses through the radial artery may apply a force against the air chamber, which causes movement of the air to be detected by a pneumatic sensor which generates a respective pulse signal. In other examples, sensors 18 may include one or more spectrophotometric sensors. A spectrophotometric sensor may be configured to emit a light of two or more wavelengths into the wrist of the patient and detect a magnitude of the wavelengths passing through tissue. As the blood pressure pulse passes through the radial artery, and other arteries of the wrist, the volume of arterial blood increases with each pulse and decreases between pulses. The change in the ratio of detected light intensity of the two or more wavelengths is representative of this change in blood volume with each pulse. Therefore, the pulse information generated by a spectrophotometric sensor may include a photoplethysmogram or include information associated with a photoplethysmogram. Although pneumatic pulse sensors and spectrophotometric sensors are described as example types of sensors for sensors 18, sensors 18 may utilize any type of sensor configured to detect pulses of blood through arteries of the patient.

Each of sensors 18 are coupled to pulse monitoring device 16 via respective cables 20A and 20B in the example of FIG. 1. Pulse monitoring device 16 may provide electrical power to sensors 18 and/or receive transmitted pulse signals from each of sensors 18. Therefore, cables 20A and 20B may include electrical wires to carry these electrical signals. In other examples, one or more of sensors 18 may be separate device configured to wirelessly transmit pulse information to pulse monitoring device 16 and/or patient evaluation device 22, in some examples, such as when sensors 18 include a pneumatic pulse sensor, cables 20A and 20B may be constructed with a sealed lumen containing a gas (e.g., air, nitrogen, or other gas) that transmits changes to volume in a cuff on the wrist through the respective cable 20 and to pulse monitoring device 16 for detection. In this manner, sensors 18 may include electronic components and/or provide a medium through which the blood pressure pulses from wrists 14 can be detected at pulse monitoring device 16. Although a single pulse monitoring device 16 is shown to communicate with sensors 18 in the example of FIG. 1, in other examples each sensor 18 may communicate with a respective pulse monitoring device similar the pulse monitoring device 16.

The pulse information generated by sensors 18 and/or pulse monitoring device 16 is therefore representative of a pulse waveform of blood within one or more arteries of patient 12 and detectable at different locations from each wrist 14. Each location on each of wrists 14 may be associated with a respective organ of the patient, such as a kidney, a liver, a spleen, a heart, and a lung. For example, on right wrist 14A, the blood pressure pulse closest to the right hand, or the distal end of wrist 14A, may be indicative of the lungs, with a location proximal of the lungs location being indicative of the spleen, and a location proximal of the spleen location being indicative of the kidney. On left wrist 14B, the blood pressure pulse closest to the left hand, or the distal end of wrist 14B, may be indicative of the heart, with a location proximal of the heart location being indicative of the liver, and a location proximal of the liver location being indicative of the kidney. In some examples, the location on the right and left wrists indicative of kidneys are indicative for kidneys in general (e.g., neither location on each wrist is specific for a left or right kidney). According to acupuncture terminology, these three locations along the radial artery of each wrist may be referred to as the "cun," "guan," and "chi" positions starting from the distal end of each wrist. Therefore, the "cun" position is closest to the base of the thumb, and the "chi" position is the most proximal of the locations.

The pulse information may include one or more characteristics of the pulse, such as one or more of a pulse rate, a pulse amplitude, a pulse wave velocity, a pulse rate variability, a pulse waveform morphology, or a pulse echo. A pulse rate is the rate, or frequency, at which consecutive pulses of blood travel through an artery. The pulse amplitude is the strength or magnitude of the pulse that may be represented as an absolute pressure, relative pressure to atmospheric or baseline pressure, or percentage increase over a baseline amplitude, for example. A pulse wave velocity indicates the speed at which the pulse travels through the artery. A pulse rate variability is a representation of how the pulse rate changes over time. A pulse waveform morphology may indicate a shape or feature of the pulse waveform, such as a width of the pulse peak, the slope of the front side and/or back side of the pulse wave, a sharpness of the peak, how many peaks are detected within the pulse wave, one or more notches or interruptions in the pulse wave, or any other feature indicate of the shape of the pulse wave. The pulse echo may be a feature in the pulse wave that is caused by one or more reflected pressure waves within the artery, which may, in some examples, be detected as one or more inflection points in the pulse wave or multiple peaks, humps, or bumps within a single pulse wave.

In some examples, the pulse information may represent each of these characteristics by way of an analog signal representative of the pulse waveform detected from patient 12. Therefore, pulse monitoring device 16 and/or patient evaluation device 22 may analyze the analog signal to extract these features of the pulse waveform. In other examples, the pulse information may already include determined values or another representation of one or more of these characteristics.

Pulse monitoring device 16 may be configured to process the pulse information received from sensors 18 or generate the pulse information based on pulse signals received from sensors 18. For example, pulse monitoring device 16 may include signal conditioning circuitry (e.g., signal conditioning circuitry 68 in FIG. 3) that may include one or more filters, an analog to digital converter, amplifiers, and the like. In some examples, pulse monitoring device 16 may analyze the pulse signal, conditioned pulse signal, or pulse information. For example, pulse monitoring device 16 may generate one or more of the characteristics of the pulse signal for transmission to patient evaluation device 22 as at least part of the pulse information. In this manner, pulse monitoring device 16 may perform none, some, or all of the analysis of the pulse signal or pulse information received from sensors 18. In any case, pulse monitoring device 16 may transmit the pulse information to patient evaluation device 22 via wired or wireless transmission protocols. In some examples, patient evaluation device 22 may include pulse monitoring device 16 or components configured to perform the functions attributed to pulse monitoring device 16 herein.

Patient evaluation device 22 may receive the pulse information from pulse monitoring device 16 and apply at least part of the pulse information to a deep learning model or algorithm trained to generate a score indicative of renal denervation efficacy in treating hypertension for patient 12. The pulse information applied to the deep learning model may include values of one or more characteristics of the pulse waveform detected from patient 12. In addition to the pulse information, patient evaluation device 22 may apply values of respective patient metrics to the deep learning model as inputs to the deep learning model. The patient metrics may include characteristics of patient 12, other than pulse information, that may be informative of whether or not renal denervation stimuli may provide a therapeutic benefit for patient 12 suffering from hypertension. These patient metrics may include one or more of an age of the patient, a gender of the patient, an ethnic background of the patient, a weight of the patient, a height of the patient, a diet of the patient, an activity level of the patient, or a stress level of the patient. Other patient metrics may additionally or alternatively be used in other examples. In some examples, patient evaluation device 22 may apply all of these patient metrics as inputs to the deep learning model. Respective weights may be applied to each of the patient metrics and pulse information inputs applied to the deep learning model.

The deep learning model may be a deep learning algorithm that leverages machine learning to establish a relationship of the pulse information and patient metrics to known renal denervation efficacy in reducing hypertension. In some examples, the deep learning model may include a deep neural network, a deep belief networks, or a recurrent neural network. In the example of the deep learning model being a neural network, the neural network may include three or more layers including an input layer, a hidden layer, and an output layer comprising a transfer function. The hidden layer may include weights applied to the inputs (e.g., the pulse information and the patient metrics). Patient evaluation device 22 may train the neural network using data from other patients to adjust each of the weights applied to the respective inputs. The sum of the weighted inputs may then be applied to the transfer function to generate and output a score or other indication of whether or not renal denervation may be effective in lowering the blood pressure of patient 12.

Patient evaluation device 22 may, in some examples, compare the score to a threshold. This comparison may determine whether or not the score indicates that patient 12 may benefit from renal denervation therapy or whether renal denervation therapy will not meaningfully reduce blood pressure. In other words, in some examples, the threshold may be set to a value indicative of a threshold reduction in blood pressure that defines renal denervation efficacy. In some examples, the score may include a percentage of hypertension in patient 12 that is associated with kidney function. Based on this percentage, patient evaluation device 22 or a clinician may determine whether or not the kidneys are contributing to hypertension such that renal denervation will effectively reduce the blood pressure of patient 12 to a target level. The target level may be a systolic and/or diastolic blood pressure level or a reduction in a hypertensive systolic and/or diastolic pressure, for example.

In other examples, the score generated by patient evaluation device 22 may be or include a probability that patient 12 would achieve a target reduction in hypertension (e.g., a reduction in hypertensive blood pressures) in response to receiving renal denervation therapy. This probability of achieving the target reduction in hypertension may be based on a single target, such as a specific blood pressure value or a specific reduction in blood pressure values. In other examples, score may include multiple probabilities of renal denervation achieving respective blood pressure values. For example, the score may include different probabilities of achieving different magnitude reductions in systolic pressure (e.g., 5 mmHg, 15 mmHg, and 25 mmHg). In this manner, the score may provide guidance to a clinician as to whether or not renal denervation may reduce hypertensive blood pressures for patient 12 and a likelihood of how much of a reduction in blood pressure patient 12 could expect to achieve.

Patient evaluation device 22 may present a graphical user interface via a display or other device configured to provide feedback to a clinician. Via the graphical user interface, patient evaluation device 22 may present the score and/or other information associated with the score that is indicative of renal denervation efficacy in reducing hypertension for patient 12. In some examples, patient evaluation device 22 may be configured to receive user input via the user interface that provides values for one or more patient metrics used by patient evaluation device 22 to generate the score.

Figure 2:
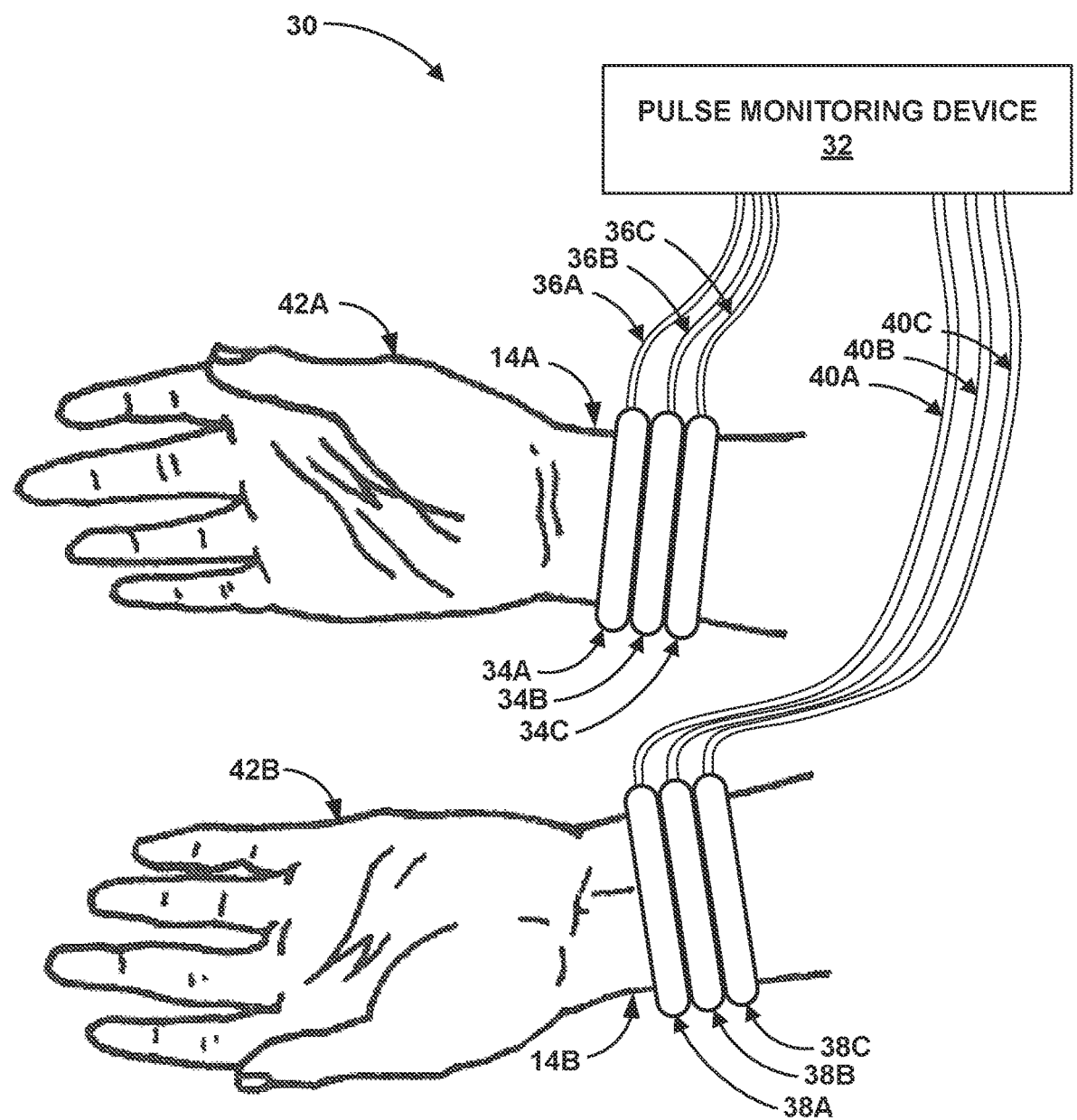
FIG. 2 is a conceptual illustration of an example pulse monitoring device coupled to pulse sensors positioned on the wrists of the patient.

FIG. 2 is a conceptual illustration of an example pulse monitoring device 32 coupled to pulse sensors 34A, 34B, and 34C (collectively "pulse sensors 34") and pulse sensors 38A, 38B, and 38C (collectively "pulse sensors 38") positioned on the wrists 14 of the patient 12. Pulse detection system 30 includes pulse monitoring device 32 and pulse sensors 34 and 38. Pulse monitoring device 32 may be an example of pulse monitoring device 16 of FIG. 1, and pulse sensors 34 and 38 may be an example of sensors 18A and 18B. Cables 36A, 36B, and 36C (collectively "cables 36") and cables 40A, 40B, and 40C (collectively "cables 40") may be similar to cables 20 of FIG. 1.

In the example of FIG. 2, pulse sensors 34 and 38 include three different sensing modules. These three different sensing modules, such as pulse sensors 34A, 34B, and 34C, are configured to be placed at different axial locations along the respective one of wrists 14. In this manner, each of the sensing modules can be located to detect a pulse wave at different locations of the wrist. In this manner, each of the different sensing modules of sensors 34 and 38 may be configured to generate respective signals representative of pulses from respective locations along the respective wrist of the patient. The pulse information from each of sensors 34 and 38 may be representative or include the respective signals from each of the sensor modules.

In this manner, sensors 34 and 38 are configured to generate pulse information representative of a pulse waveform of blood within one or more arteries and detectable at different locations from each wrist 14. For example, pulse sensors 34 located on wrist 14A may be configured such that sensor module 34A closest to right hand 42A detects pulse waves indicative of aspects of the lungs such as lung function, sensor module 34B detects pulse waves indicative of aspects of the spleen such as spleen function, and sensor module 34C detects pulse waves indicative of aspects of the kidney such as kidney function. On left wrist 14A, sensor module 38A disposed closest to left hand 42B detects pulse waves indicative of aspects of the heart such as heart function, sensor module 38B detects pulse waves indicative of aspects of the liver such as liver function, and sensor module 38C detects pulse waves indicative of aspects of the kidney such as kidney function. In this manner, pulse sensors 34 and 38 may provide pulse information from three locations of each wrist 14 at the same time and at the target wrist locations.

In the example of FIG. 2, each of pulse sensors 34 and 38 include pneumatic pulse sensor modules. Each module of pulse sensor 34 is connected to a respective pneumatic tube of cables 36, and each module of pulse sensor 38 is connected to a respective pneumatic tube of cables 40. In this manner, pulse monitoring device 32 may separately control each module of pulse sensors 34 and 38. For example, pulse monitoring device 32 may control the air pressure within each of pulse sensors 34 and 38 and detect variations in the air pressure that result from each passing pulse wave of the blood within the radial arteries. Pulse monitoring device 32 may generate an electrical signal representative of the air pressure variations, condition the electrical signals, and analyze the electrical signals to generate pulse information for each of the locations of wrists 14A corresponding to the placement of pulse sensors 34 and 38. Pulse monitoring device 32 may then transmit the pulse information for evaluation using a deep learning model, such as transmission to patient evaluation device 22 of FIG. 1.

In some examples, each of the sensing modules, such as sensing modules 34A, 34B, and 34C, are constructed at a set (e.g., predetermined and prefixed) spacing from each other along the axial length of the wrist. In other examples, the sensing modules of sensors 34 and 38 may be separate from each other or movable with respect to each other in order to place the sensing modules as the appropriate locations of patients with different sized wrists.

Although the example of FIG. 2 is directed to pneumatic sensing modules that convert air pressure to pulse information, pulse sensors 34 and 38 may alternatively, or additionally, include other types of sensors directed to other types of mediums and transformations of energy. For example, sensors 34 and 38 may include modules that include spectrophotometric sensors that emit light at different wavelengths and detect the magnitude of the light at each wavelength passing through the tissue of wrists 14. This type of sensor may be similar to pulse oximetry sensing systems. In other examples, mechanical sensors such as accelerometers may be used to detect pulse waves and transform that mechanical movement to electrical signals that are processed to represent the pulse waves. In this manner, sensors 34 and 38 may include one or more types of sensors that are configured to generate pulse information representative of detected blood pressure pulse waves traveling through one or more arteries of wrists 14. As discussed above, this pulse information may be indicative of kidney function associated with hypertension.

Figure 3:
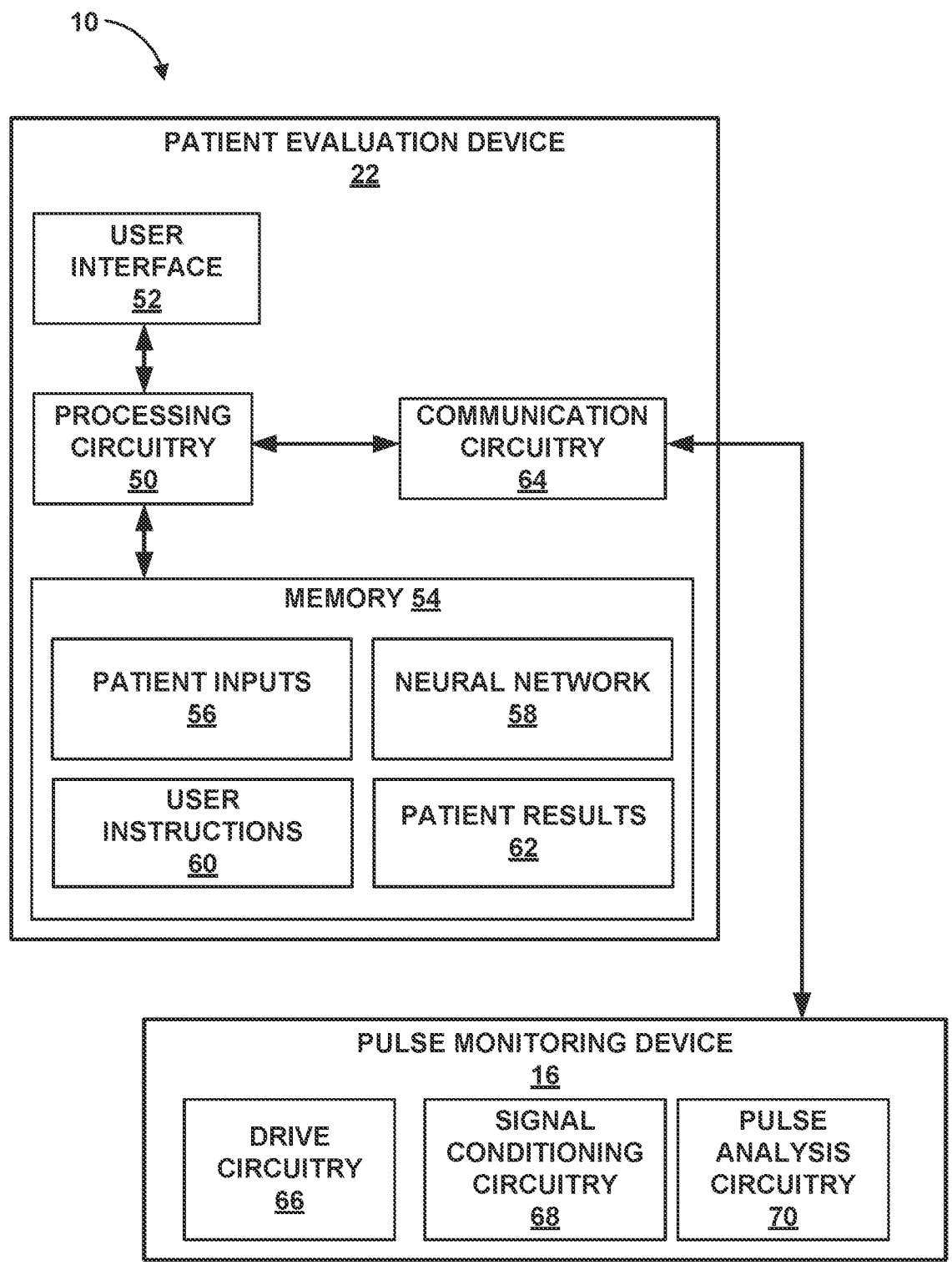
FIG. 3 is a block diagram of an example patient evaluation device in communication with a pulse monitoring device.

FIG. 3 is a block diagram of an example patient evaluation device 22 in communication with an example pulse monitoring device 16. While various circuitries, algorithms, modules, and functions are described with reference to patient evaluation device 22 and pulse monitoring device 16 of FIG. 3, in other examples, patient evaluation device 22 and pulse monitoring device 16 may distribute functionality differently or one or more other devices may provide functionality instead, or in addition to, patient evaluation device 22 and/or pulse monitoring device 16.

In the example of FIG. 3, patient evaluation device 22 includes processing circuitry 50, user interface 52, memory 54, and communication circuitry 64. Memory 54 includes computer-readable instructions that, when executed by processing circuitry 50, causes patient evaluation device 22 to perform various functions. Processing circuitry 50 may include any one or more microprocessors, controllers, digital signal processors (DSPs), application specific integrated circuits (ASICs), field-programmable gate arrays (FPGAs), or equivalent discrete or integrated digital or analog logic circuitry, and the functions attributed to processing circuitry 50 herein may be embodied as software, firmware, hardware or any combination thereof.

Memory 54 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media. Memory 54 may store any suitable information, including patient identification information, pulse information, information for analyzing the pulse information, and information related to generating a score indicative of whether or not renal denervation therapy would be effective to treat a patient having hypertension. For example, memory 54 may store one or more of patient inputs 56, neural network 58, user instructions 60, and patient results 62 in separate memories within memory 54 or separate areas within memory 54.

Patient inputs 56 may store values of patient metrics specific to one or more patients, patient identification information, or any other information specific to a patient being evaluated for renal denervation therapy. Neural network 58 may include the deep learning model or algorithm trained to establish a relationship of pulse information and patient metrics to renal denervation efficacy for treating hypertension. In some examples, neural network 58 may define each of the layers of a neural network, weights for each node of each layer, a transfer function, and any other information associated with the neural network or other deep learning model utilized by patient evaluation device 22. Neural network 58 may be a trained deep learning model such that processing circuitry 50 can obtain the neural network 58 and apply the pulse information and values of patient metrics for the patient to neural network 58 to obtain a score indicative of renal denervation efficacy.

User instructions 60 may include instructions for a clinician on which patient metrics need to be obtained, how to operate pulse monitoring device 16, how to interpret the score output by patient evaluation device 22, or any other actions associated with the operation of patient evaluation device 22. Patient results 62 may include the scores generated for one or more patients. Patient results 62 may be stored in a secured repository for patient privacy or deleted after transfer to a different device.

A user, such as a clinician or patient, may interact with processing circuitry 50 through user interface 52. User interface 52 may include a display, such as a liquid crystal display (LCD), light-emitting diode (LED) display, or other screen, to present information related to obtaining pulse information, obtaining patient metrics, and/or the score generated by processing circuitry 50, and buttons or a pad to provide input to patient evaluation device 22. Buttons of user interface 52 may include an on/off switch, plus and minus buttons to zoom in or out or navigate through options, a select button to pick or store an input, and pointing device, e.g. a mouse, trackball, or stylus. Other input devices may be a wheel to scroll through options or a touch pad to move a pointing device on the display. In some examples, the display may include a touch-sensitive display or presence-sensitive display that enables the user to select options directly from interaction with the display.

In some examples, patient evaluation device 22 may include communication circuitry 64 configured to support wired and/or wireless communication between patient evaluation device 22 and pulse monitoring device 16 or another computing device under the control of processing circuitry 50. For example, patient evaluation device 22 may communicate with pulse monitoring device 16 over a wired and/or wireless network via communication circuitry 64. Patient evaluation device 22 may be a networked server in other examples such that users may access patient evaluation device 22 over a network connection via pulse monitoring device 16 and/or another computing device. In other examples, patient evaluation device 22 may take the form of a workstation, notebook computer, hand-held computer, tablet computer, mobile phone, or any other computing device. In some examples, patient evaluation device 22 and/or pulse monitoring device 16 may be a part of a renal denervation therapy device configured to deliver the renal denervation therapy to the patient after the generated score indicates renal denervation would be effective in treating hypertension of the patient.

Patient evaluation device 22 may be configured to communicate with pulse monitoring device 16 via communication circuitry 64. Pulse monitoring device 16 may control patient evaluation device 22, patient evaluation device 22 may control pulse monitoring device 16, or each device may request and transmit information as needed to perform the functions described herein. In some examples, pulse monitoring device 16 includes drive circuitry 66, signal conditioning circuitry 68, and pulse analysis circuitry 70. For example, drive circuitry 66 may provide operational power and/or mechanical functionality to one or more sensors (e.g., sensors 18, 34, or 38). In this manner, drive circuitry 66 may be configured to control each of the sensors configured to generate pulse signals from the wrists of the patient. However, in other examples, the sensors (e.g., sensors 18) may operate independently and transmit pulse signals or pulse information directly to pulse monitoring device 16 and/or patient evaluation device 22.

Signal conditioning circuitry 68 is configured to receive pulse signals from sensors 18, for example, and condition the pulse signals. For example, signal conditioning circuitry 68 may apply one or more analog and/or digital filters to the pulse signals, amplify the pulse signals, convert analog signals to digital signals, or perform any other conditioning function appropriate for the received pulse signals. Pulse analysis circuitry 70 may analyze the conditioned pulse signal for one or more characteristics of the pulse signal to generate pulse information. For example, pulse analysis circuitry 70 may generate characteristics of the pulse wave detected from different locations of the wrists such as a pulse rate, a pulse amplitude, a pulse wave velocity, a pulse rate variability, a pulse waveform morphology, and/or a pulse echo. In other examples, pulse monitoring device 16 may transmit pulse information to patient evaluation device 22 as the raw or conditioned pulse signals.

Figure 4:
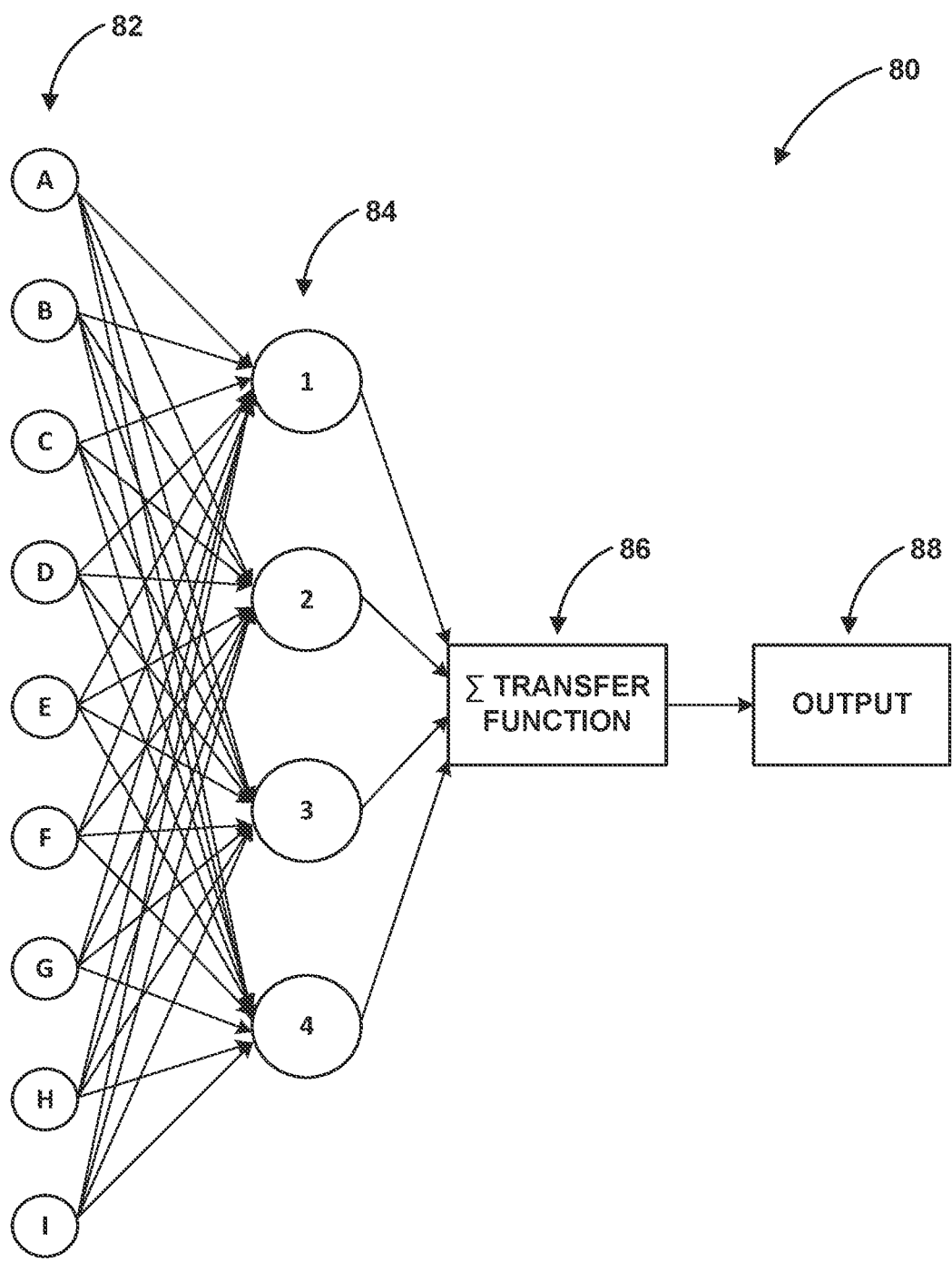
FIG. 4 is a conceptual diagram illustrating an example neural network configured to predict renal denervation therapy efficacy for a patient with hypertension.

FIG. 4 is a conceptual diagram illustrating an example neural network 80 configured to predict renal denervation therapy efficacy for a patient diagnosed with hypertension. Neural network 80 is an example of a deep learning model, or deep learning algorithm, trained to generate a score indicative of renal denervation therapy efficacy. As discussed above, other types of machine learning and deep learning models or algorithms may be utilized in other examples. Patient evaluation device 22 may train, store, and/or utilize neural network 80, but other devices may apply inputs associated with a particular patient to neural network 80 in other examples. Neural network 80 is an example of neural network 58 (FIG. 3), which may be stored by patient evaluation device 22.

As shown in the example of FIG. 4, neural network 80 comprises three layers. These three layers include input layer 82, hidden layer 84, and output layer 86. Output layer 88 comprises the output from the transfer function of output layer 86. Input layer 82 represents each of the input values A through I provided to neural network 80. The input values may be values for patient metrics such as an age of the patient, a gender of the patient, an ethnic background of the patient, a weight of the patient, a height of the patient, a diet of the patient, an activity level of the patient, and/or a stress level of the patient. The input values may be numerical or categorical as appropriate for each patient metric. In some examples, values for all of these patient metrics may be incorporated into neural network 80.

In addition, some input values of input layer 82 may include one or more characteristics of the pulse information obtained from the wrists of the patient. For example, the characteristics may include at least one of a pulse rate, a pulse amplitude, a pulse rate variability, a pulse waveform morphology, or a pulse echo. These characteristics may be input into input layer 82 for each location along each wrist. In some examples, the characteristics, such as pulse waveform morphology may be converted to a numerical value or some other input representative of the type of waveform identified from the pulse wave of the blood in the patient.

Each of the input values for each node in the input layer 82 is provided to each node of hidden layer 84. In the example of FIG. 4, hidden layer 84 include four nodes, but fewer or greater number of nodes may be used in other examples. Each input from input layer 82 is multiplied by a weight and then summed at each node of hidden layer 84. During training of neural network 80, the weights for each input are adjusted to establish the relationship between the pulse information and patient metrics to renal denervation efficacy. In some examples, two or more hidden layers may be incorporated into neural network 80, where each layer includes the same or different number of nodes.

The result of each node within hidden layer 84 is applied to the transfer function of output layer 86. The transfer function may be liner or non-linear, depending on the number of layers within neural network 80. Example non-linear transfer functions may be a sigmoid function or a rectifier function. The output 88 of the transfer function may be the score that is generated by patient evaluation device 22 in response to applying the pulse information and patient metric values for the patient to neural network 80. A deep learning model, such as neural network 80, may enable a computing system such as patient monitoring device 22 to screen patients for renal denervation therapy using a variety of values representing the condition of a particular patient.

Figure 5:
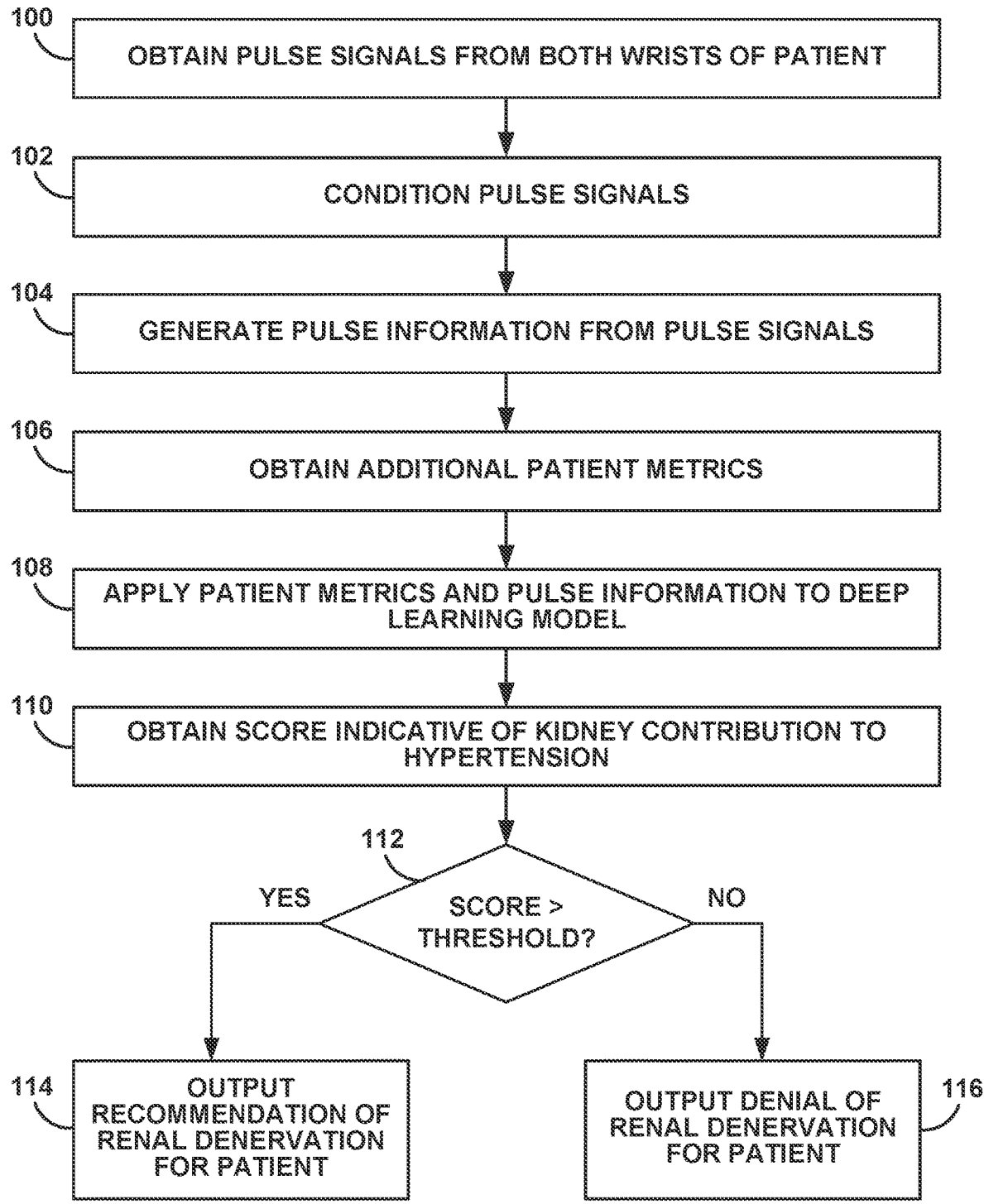
FIG. 5 is a flow diagram illustrating an example technique for generating a score indicative of renal denervation efficacy for treating hypertension of a patient.

FIG. 5 is a flow diagram illustrating an example technique for generating a score indicative of a predicted renal denervation efficacy for treating hypertension of a patient. The example technique of FIG. 5 is described with reference to the example system 10 of FIG. 1, such as patient evaluation device 22 and pulse monitoring device 16. However, any suitable systems or devices may perform these techniques in other examples, such as pulse monitoring device 32.

As shown in the example of FIG. 5, pulse monitoring device 16 obtains pulse signals from both wrists 14 of patient 12 (100). For example, sensors 18 may generate the pulse signals representative of pulse waves of blood within a radial artery of each of wrists 14 and transmit those pulse signals to pulse monitoring device 16. Signal conditioning circuitry 68 of pulse monitoring device 16 then conditions the pulse signals (102), and pulse analysis circuitry 70 generates pulse information from the conditioned pulse signals (104). Pulse monitoring device 16 may then transmit the pulse information to processing circuitry 50 of patient monitoring device 22. The pulse information may include characteristics of pulse waves represented by the pulse signals, where each characteristic may include information associated with kidney function in relation to regulating blood pressure for the patient. In other examples, pulse monitoring device 16 may include the conditioned pulse signals as, or as a part of, the pulse information transmitted to processing circuitry 50. In this example, processing circuitry 50 may analyze the pulse signals to extract one or more characteristics of the pulse signals.

In addition to obtaining the pulse information, processing circuitry 50 obtains additional values of patient metrics of patient 12 (106). For example, processing circuitry 50 may retrieve the patient metric values from patient inputs 56 of memory 54, or processing circuitry 50 may control user interface 52 to prompt the clinician or user to enter unknown patient metric values. Processing circuitry 50 then applies the patient metric values and the pulse information to a deep learning model (108). For example, processing circuitry 50 may utilize neural network 80 described in the example of FIG. 4. Processing circuitry 50 the obtains a score from the deep learning model that indicates kidney contribution to hypertension (110). For example, a higher score indicating that the patient's kidneys are functioning to contribute to higher systemic blood pressure suggests that renal denervation therapy that modulates such kidney function may provide a target decrease in systemic blood pressures for that patient. In other examples, the score may be a probability of renal denervation efficacy or some other measure of suitability of renal denervation for treating a patient suffering from hypertension.

For example, if the score is greater than a threshold ("YES" branch of block 112), processing circuitry 50 outputs a recommendation of renal denervation for the patient (114). In the score is less than or equal to the threshold ("NO" branch of block 112), processing circuitry 50 may output a denial, or non-recommendation, of renal denervation for the patient (116). The threshold may be set to a value where a score exceeding the threshold indicates a target reduction in blood pressure would likely be met as a result of renal denervation. For example, if the score is a reduction in blood pressure in mmHg, the threshold may be set to values such as 5, 10, 15, 20, 25, or 30 mmHg. A clinician may set the threshold based on the severity of the patient's hypertension. In some examples, processing circuitry 50 may output the score alone, or the score and the threshold instead of providing a recommendation to the clinician.

In other examples, processing circuitry 50 may output a plurality of scores that indicate a probability that renal denervation will achieve respective reductions in blood pressure values. For example, the output may include three probabilities of efficacy, where each probability is tired to a specific mmHg reduction in blood pressure (e.g., 10 mmHg, 20 mmHg, and 30 mmHg). In some examples, a clinician may set each target blood pressure value and/or the number of blood pressure values to customize the output of patient monitoring device 22 for the specific patient.

The following are examples of subject matter described herein. Example 1: a system comprising a memory configured to store a deep learning model, the deep learning model trained to represent a relationship of pulse information and patient metrics to renal denervation efficacy in reducing hypertension; and processing circuitry configured to: obtain pulse information representative of pulses from one or more wrists of a patient; obtain a plurality of values representative of respective patient metrics for the patient; apply the pulse information and the plurality of values to the deep learning model from the memory; responsive to applying the pulse information and the plurality of values to the deep learning model, obtain, from the deep learning model, a score indicative of renal denervation efficacy in reducing hypertension for the patient; and generate a graphical user interface comprising a graphical representation of the score for the patient.

Example 2: the system of example 1, wherein the processing circuitry is configured to compare the score to a threshold.

Example 3: the system of any of examples 1 and 2, wherein the score comprises a percentage of hypertension in the patient that is associated with kidney function.

Example 4: the system of any of examples 1 through 3, wherein the score comprises a probability that the patient would achieve a target reduction in hypertension in response to receiving renal denervation therapy.

Example 5: the system of any of examples 1 through 4, wherein the patient metrics for the patient comprise one or more of: an age of the patient, a gender of the patient, an ethnic background of the patient, a weight of the patient, a height of the patient, a diet of the patient, an activity level of the patient, or a stress level of the patient.

Example 6: the system of any of examples 1 through 5, wherein the deep learning model comprises a neural network.

Example 7: the system of example 6, wherein the neural network comprises three layers including an input layer, a hidden layer, and an output layer comprising a transfer function.

Example 8: the system of any of examples 1 through 7, wherein the pulse information comprises at least one of: a pulse rate, a pulse amplitude, a pulse wave velocity, a pulse rate variability, a pulse waveform morphology, or a pulse echo.

Example 9: the system of any of examples 1 through 8, wherein the pulse information comprises pulse information representative of a pulse waveform detectable at different locations from each wrist of the one or more wrists, wherein each location of the different locations is associated with a respective organ of the patient, and wherein the respective organs comprise a kidney, a liver, a spleen, a heart, and a lung.

Example 10: the system of any of examples 1 through 9, wherein the pulse information comprises first pulse information and second pulse information, and wherein the system further comprises: a first sensor configured to generate the first pulse information representative of pulses from a first wrist of the one or more wrists of the patient and transmit the first pulse information to the processing circuitry; and a second sensor configured to generate the second pulse information representative of pulses from a second wrist of the one or more wrists of the patient and transmit the second pulse information to the processing circuitry.

Example 11: the system of example 10, wherein: the first sensor comprises three alpha sensing modules configured to generate respective signals representative of pulses from respective locations along the first wrist of the one or more wrists of the patient, and wherein the first pulse information comprises information representative of the respective signals from the three alpha sensing modules; and the second sensor comprises three beta sensing modules configured to generate respective signals representative of pulses from respective locations along the second wrist of the one or more wrists of the patient, and wherein the second pulse information comprises information representative of the respective signals from the three beta sensing modules.

Example 12: the system of any of examples 10 and 11, wherein the first sensor and the second sensor each comprise a respective pneumatic pulse sensor.

Example 13: the system of any of examples 10 through 12, wherein the first sensor and the second sensor each comprise a respective spectrophotometric sensor.

Example 14: the system of any of examples 1 through 13, further comprising a display configured to present the graphical user interface comprising the graphical representation of the score for the patient.

Example 15: a method comprising: obtaining, by processing circuitry, pulse information representative of pulses from one or more wrists of a patient; obtaining, by the processing circuitry, a plurality of values representative of respective patient metrics for the patient; applying, by the processing circuitry, the pulse information and the plurality of values to a deep learning model stored in a memory, the deep learning model trained to represent a relationship of the pulse information and the patient metrics to renal denervation efficacy in reducing hypertension; responsive to applying the pulse information and the plurality of values to the deep learning model, obtaining, by the processing circuitry and from the deep learning model, a score indicative of renal denervation efficacy in reducing hypertension for the patient; and generating, by the processing circuitry, a graphical user interface comprising a graphical representation of the score for the patient.

Example 16: the method of example 15, further comprising comparing the score to a threshold.

Example 17: the method of any of examples 15 and 16, wherein the score comprises a percentage of hypertension in the patient that is associated with kidney function.

Example 18: the method of any of examples 15 through 17, wherein the score comprises a probability that the patient would achieve a target reduction in hypertension in response to receiving renal denervation therapy.

Example 19: the method of any of examples 15 through 18, wherein the patient metrics for the patient comprise one or more of: an age of the patient, a gender of the patient, an ethnic background of the patient, a weight of the patient, a height of the patient, a diet of the patient, an activity level of the patient, or a stress level of the patient.

Example 20: the method of any of examples 15 through 19, wherein the deep learning model comprises a neural network.

Example 21: the method of example 20, wherein the neural network comprises three layers including an input layer, a hidden layer, and an output layer comprising a transfer function.

Example 22: the method of any of examples 15 through 21, wherein the pulse information comprises at least one of: a pulse rate, a pulse amplitude, a pulse wave velocity, a pulse rate variability, a pulse waveform morphology, or a pulse echo.

Example 23: the method of any of examples 15 through 22, wherein the pulse information comprises pulse information representative of a pulse waveform detectable at different locations from each wrist of the one or more wrists, wherein each location of the different locations is associated with a respective organ of the patient, and wherein the respective organs comprise a kidney, a liver, a spleen, a heart, and a lung.

Example 24: the method of any of examples 15 through 23, wherein the pulse information comprises first pulse information and second pulse information, and wherein the method further comprises: generating, by a first sensor, the first pulse information representative of pulses from a first wrist of the one or more wrists of the patient and transmit the first pulse information to the processing circuitry; and generating, by a second sensor, the second pulse information representative of pulses from a second wrist of the one or more wrists of the patient and transmit the second pulse information to the processing circuitry.

Example 25: the method of example 24, wherein: generating the first pulse information comprises generating, by three alpha sensing modules of the first sensor, respective signals representative of pulses from respective locations along the first wrist of the one or more wrists of the patient, and wherein the first pulse information comprises information representative of the respective signals from the three alpha sensing modules; and generating the second pulse information comprises generating, by three beta sensing modules of the second sensor, respective signals representative of pulses from respective locations along the second wrist of the one or more wrists of the patient, and wherein the second pulse information comprises information representative of the respective signals from the three beta sensing modules.

Example 26: the method of any of examples 24 and 25, wherein: generating the first pulse information comprises generating the first pulse information by a first pneumatic pulse sensor; and generating the second pulse information comprises generating the second pulse information by a second pneumatic pulse sensor.

Example 27: the method of any of examples 24 through 26, wherein: generating the first pulse information comprises generating the first pulse information by a first spectrophotometric sensor; and generating the second pulse information comprises generating the second pulse information by a second spectrophotometric sensor.

Example 28: the method of any of examples 15 through 27, further comprising displaying, via a display, the graphical user interface comprising the graphical representation of the score for the patient.

Example 29: a non-transitory computer-readable medium, comprising instructions that, when executed, cause at least one processor to: obtain pulse information representative of pulses from one or more wrists of a patient; obtain a plurality of values representative of respective patient metrics for the patient; apply the pulse information and the plurality of values to the deep learning model from a memory, the deep learning model trained to represent a relationship of the pulse information and patient metrics to renal denervation efficacy in reducing hypertension; responsive to applying the pulse information and the plurality of values to the deep learning model, obtain, from the deep learning model, a score indicative of renal denervation efficacy in reducing hypertension for the patient; and generate a graphical user interface comprising a graphical representation of the score for the patient.

Example 30: a system comprising: means for obtaining pulse information representative of pulses from one or more wrists of a patient; means for obtaining a plurality of values representative of respective patient metrics for the patient; means for applying the pulse information and the plurality of values to a deep learning model stored in a memory, the deep learning model trained to represent a relationship of the pulse information and the patient metrics to renal denervation efficacy in reducing hypertension; means for obtaining from the deep learning model a score indicative of renal denervation efficacy in reducing hypertension for the patient; and means for generating a graphical user interface comprising a graphical representation of the score for the patient.

The techniques described in this disclosure may be implemented, at least in part, in hardware, software, firmware, or any combination thereof. For example, various aspects of the described techniques may be implemented within processing circuitry, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit including hardware may also perform one or more of the techniques of this disclosure.

Such hardware, software, and firmware may be implemented within the same device or within separate devices to support the various techniques described in this disclosure. In addition, any of the described instructions, units, modules or components may be implemented together or separately as discrete but interoperable logic devices. Depiction of different features as modules or units is intended to highlight different functional aspects and does not necessarily imply that such modules or units must be realized by separate hardware, firmware, or software components. Rather, functionality associated with one or more modules or units may be performed by separate hardware, firmware, or software components, or integrated within common or separate hardware, firmware, or software components.

The techniques described in this disclosure may also be embodied or encoded in a computer system-readable medium, such as a computer system-readable storage medium, containing instructions. Instructions embedded or encoded in a computer system-readable medium, including a computer system-readable storage medium, may cause one or more programmable processors, or other processors, to implement one or more of the techniques described herein, such as when instructions included or encoded in the computer system-readable medium are executed by the processing circuitry. Computer system readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or other computer system readable media. In some examples, an article of manufacture may comprise one or more computer system-readable storage media, for example, non-transitory computer system-readable storage media.

Various examples have been described. These and other examples are within the scope of the following claims.

What is claimed is:

1. A system comprising:
   a memory configured to store a deep learning model, the deep learning model trained to represent a relationship of pulse information and patient metrics to renal denervation efficacy; and
   processing circuitry configured to:
      obtain pulse information representative of pulses of a patient;
      obtain a plurality of values representative of respective patient metrics for the patient;
      apply the pulse information and the plurality of values to the deep learning model;
      responsive to applying the pulse information and the plurality of values to the deep learning model, obtain, from the deep learning model, a score indicative of renal denervation efficacy for the patient; and
      output an indication of the score indicative of renal denervation efficacy for the patient.

2. The system of claim 1, wherein the processing circuitry is configured to:
   compare the score to a threshold; and
   output an indication the patient would likely benefit from renal denervation therapy in response to determining the score is greater than or equal to the threshold.

3. The system of claim 1, wherein the score comprises a percentage of hypertension in the patient that is associated with kidney function.

4. The system of claim 1, wherein the score comprises a probability that the patient would achieve a target reduction in hypertension in response to receiving renal denervation therapy.

5. The system of claim 1, wherein the patient metrics for the patient comprise one or more of: an age of the patient, a gender of the patient, an ethnic background of the patient, a weight of the patient, a height of the patient, a diet of the patient, an activity level of the patient, or a stress level of the patient.

6. The system of claim 1, wherein the pulse information comprises at least one of: a pulse rate, a pulse amplitude, a pulse wave velocity, a pulse rate variability, a pulse waveform morphology, or a pulse echo.

7. The system of claim 1, wherein the pulse information comprises first pulse information and second pulse information, and wherein the system further comprises:
   a first sensor configured to generate the first pulse information representative of pulses from a first location of the patient and transmit the first pulse information to the processing circuitry; and
   a second sensor configured to generate the second pulse information representative of pulses from a second location of the patient and transmit the second pulse information to the processing circuitry.

8. The system of claim 7, wherein the first sensor and the second sensor each comprise a respective pneumatic pulse sensor.

9. The system of claim 7, wherein the first sensor and the second sensor each comprise a respective spectrophotometric sensor.

10. The system of claim 1, further comprising a display configured to present a graphical user interface comprising a graphical representation of the score for the patient.

11. A method comprising:
   obtaining, by processing circuitry, pulse information representative of pulses of a patient;
   obtaining, by the processing circuitry, a plurality of values representative of respective patient metrics for the patient;
   applying, by the processing circuitry, the pulse information and the plurality of values to a deep learning model, the deep learning model trained to represent a relationship of the pulse information and the patient metrics to renal denervation efficacy;
   responsive to applying the pulse information and the plurality of values to the deep learning model, obtaining, by the processing circuitry and from the deep learning model, a score indicative of renal denervation efficacy for the patient; and
   outputting, by the processing circuitry, an indication of the score indicative of renal denervation efficacy for the patient.

12. The method of claim 11, further comprising:
   comparing the score to a threshold; and
   outputting an indication the patient would likely benefit from renal denervation therapy in response to determining the score is greater than or equal to the threshold.

13. The method of claim 11, wherein the score comprises a percentage of hypertension in the patient that is associated with kidney function.

14. The method of claim 11, wherein the score comprises a probability that the patient would achieve a target reduction in hypertension in response to receiving renal denervation therapy.

15. The method of claim 11, wherein the patient metrics for the patient comprise one or more of an age of the patient, a gender of the patient, an ethnic background of the patient, a weight of the patient, a height of the patient, a diet of the patient, an activity level of the patient, or a stress level of the patient.

16. The method of claim 11, wherein the pulse information comprises at least one of: a pulse rate, a pulse amplitude, a pulse wave velocity, a pulse rate variability, a pulse waveform morphology, or a pulse echo.

17. The method of claim 11, wherein the pulse information comprises first pulse information and second pulse information, and wherein the method further comprises:
   generating, by a first sensor, the first pulse information representative of pulses from a first location of the patient and transmit the first pulse information to the processing circuitry; and
   generating, by a second sensor, the second pulse information representative of pulses from a second location of the patient and transmit the second pulse information to the processing circuitry.

18. The method of claim 17, wherein:
   generating the first pulse information comprises generating the first pulse information by a first pneumatic pulse sensor; and
   generating the second pulse information comprises generating the second pulse information by a second pneumatic pulse sensor.

19. The method of claim 11, further comprising displaying, via a display, a graphical user interface comprising a graphical representation of the score for the patient.

20. A non-transitory computer-readable medium, comprising instructions that, when executed, cause at least one processor to:
   obtain pulse information representative of pulses of a patient;
   obtain a plurality of values representative of respective patient metrics for the patient;
   apply the pulse information and the plurality of values to a deep learning model, the deep learning model trained to represent a relationship of the pulse information and patient metrics to renal denervation efficacy;
   responsive to applying the pulse information and the plurality of values to the deep learning model, obtain, from the deep learning model, a score indicative of renal denervation efficacy for the patient; and
   output an indication of the score indicative of renal denervation efficacy for the patient.

* * * * *